United States Patent
Lefevre et al.

(10) Patent No.: US 6,427,525 B1
(45) Date of Patent: Aug. 6, 2002

(54) VISCOSITY SENSOR AND REGULATOR FOR CONTINUOUSLY CONTROLLING A QUENCHING BATH

(75) Inventors: Yves Lefevre, Vandoeuvre lès Nancy; Fabrice Vanaquer, Pont Saint Vincent, both of (FR)

(73) Assignee: Process Industries, Neuves Maisons (FR)

( * ) Notice: Subject to any disclaimer, the term of this patent is extended or adjusted under 35 U.S.C. 154(b) by 0 days.

(21) Appl. No.: 09/622,563

(22) PCT Filed: Feb. 18, 1999

(86) PCT No.: PCT/FR99/00371

§ 371 (c)(1), (2), (4) Date: Oct. 2, 2000

(87) PCT Pub. No.: WO99/42808

PCT Pub. Date: Aug. 26, 1999

(30) Foreign Application Priority Data

Feb. 19, 1998 (FR) .............................................. 98 02160

(51) Int. Cl.[7] .......................... G01N 11/06; G01N 33/86
(52) U.S. Cl. ..................................... 73/54.15; 73/54.18
(58) Field of Search ........................... 73/54.14, 54.15, 73/54.13, 54.16, 54.18, 54.19, 54.21

(56) References Cited

U.S. PATENT DOCUMENTS

| | | | | |
|---|---|---|---|---|
| 1,604,409 A | * | 1/1926 | Grindrod .................... | 73/54.15 |
| 2,778,220 A | * | 1/1957 | Kuhlmann et al. ........ | 73/54.18 |
| 3,371,522 A |   | 3/1968 | Norcross .................... | 73/54.15 |
| 3,512,396 A |   | 5/1970 | Okamoto .................... | 73/54.21 |
| 3,782,174 A | * | 1/1974 | Varadi et al. ............... | 73/54.15 |
| 4,154,094 A |   | 5/1979 | Norcross .................... | 73/54.15 |
| 4,752,449 A | * | 6/1988 | Jackson et al. ............. | 73/54.15 |
| 5,569,843 A |   | 10/1996 | Poissant ..................... | 73/54.07 |
| 5,959,196 A | * | 9/1999 | Norcross et al. ............ | 73/54.18 |

FOREIGN PATENT DOCUMENTS

| | | | |
|---|---|---|---|
| EP | 0539753 | 5/1993 | |
| FR | 1465669 | 3/1967 | |
| JP | 60154141 A | * 8/1985 | ................ 73/54.19 |
| WO | WO 9811420 | 3/1998 | |

OTHER PUBLICATIONS

F. Chaouche, "Use of Aqueous Solutions as Quenching Fluid", ATTT (Technical Association for Thermic Treatment), pp. 47–55 (Lyons—Jun., 1997).

A. Mulot, "Comparisons of Quenching Environments: Performance, Conditions of Use, Criteria for Selection", Thermic Treatment Journal, No. 298, pp. 39–43 (Apr., 1997).

* cited by examiner

*Primary Examiner*—Hezron Williams
*Assistant Examiner*—Michael Cygan
(74) *Attorney, Agent, or Firm*—Gary M. Cohen

(57) ABSTRACT

A viscosity sensor operates by measuring the time taken for a piston to fall within the measuring chamber of a calibrated tube immersed in a bath, and an apparatus comprising the sensor is used for the continuous control of a quenching bath. A cam or an equivalent mechanism is used to lift a mobile assembly having a sensor in its upper part and a piston in its lower part. The sensor detects the passage of a pair of shoulders and passes the data on to a regulator for further processing.

24 Claims, 6 Drawing Sheets

VISCOSITY SENSOR AND REGULATOR FOR CONTINUOUSLY CONTROLLING A QUENCHING BATH

BACKGROUND OF THE INVENTION

This invention concerns a viscosity sensor, and a device comprising the viscosity sensor, in particular but not limited to a device for continuously controlling a quenching bath.

In a large number of applications, an industrial part needs to undergo a quenching operation after a thermic treatment to obtain the mechanical properties required for proper operation of the industrial part. Such a quenching operation can take place in various media including water, oil, dissolved salt and a water-polymer mixture.

In a typical quenching operation, the parts are first heated to a high temperature (e.g., about 900° C.). The heated parts are then cooled, down to an ambient temperature, by following a controlled cooling rate which depends on the type of fluid used for the quenching.

The power supplied to the quenching bath is called "drasticity". For quenching baths that use water, salt or oil, drasticity is ordinarily fixed, and specified by the supplier.

Polymers have the advantages that they are non-flammable, non-polluting, non-toxic, and that they are able to be washed with water. For water-polymer mixtures, drasticity depends on the type of polymers used, the concentration of the mixture, and aging of the mixture. During successive quenchings, the polymer bath loses its properties due to product aging, water evaporation, removal of the polymer from the bath by adherence to the parts, thermic effects, and the presence of metal particles and soot in the bath. For these reasons, the user must regularly monitor the quality of the polymer bath to keep the bath at its correct drasticity value.

Drasticity is presently controlled either by direct measurement of the drasticity or by indirect measurement.

Drasticity can be directly measured using a drasticimeter, a device which is capable of measuring the cooling curve of a silver-calibrated test piece immersed in a bath having known characteristics, volume and agitation. The use of a drasticimeter is the only known method which gives a true measurement of drasticity. However, this requires the use of complex equipment which is generally reserved for laboratories.

For the indirect measurement of drasticity, a parameter representing the highest possible degree of drasticity, such as refraction index or viscosity, can be measured by various means. Refraction index can be measured manually, using a refractometer, permitting rapid measurement which can be carried out in a workshop for determining the polymer concentration of the quenching bath. While this is an effective measurement, such measurements can be carried out only for a new bath. Viscosity can be measured using a viscosimeter. While this results in a more precise measurement than a manual measurement with a refractometer, viscosity measurements are exclusively carried out in the laboratory.

Consequently, the two types of indirect measurement currently used cannot be continuously effected in the quenching bath, but are instead made on samples taken from the bath.

The Hardening Fluids Commission of the A.T.T.T. (Technical Association for Thermic Treatment) recommends viscosity as the element to be monitored for purposes of monitoring aging of the polymer. Reading the refraction index is not considered very precise because it is sensitive to all types of pollution. Measurement using a Utbelhode tube is recommended, and a standard to this effect has been published (see, article-extracts of the A.T.T.—Lyons—June 1997).

To facilitate control and maintenance of the quenching bath, users need to have, in situ, a continuous measuring system for regulating the quality of the bath. However, no method for the continuous control of the drasticity or viscosity of a quenching bath is currently known (see, Quenching file—Thermic Treatment Journal—1997). Viscosimeters that can operate continuously are used in other fields of application, such as for foodstuffs, resins, paints and other materials, but none is adaptable to the field of thermic treatment or sufficiently sensitive to provide the required values and precision.

The object of the present invention is to develop a viscosity sensor and a measurement device that can satisfy the specific needs for continuously controlling polymer baths used for quenching parts and that is strong enough to withstand the working conditions in forges and smelting works, that exhibits no drift or wear, that functions with a simple energy element, and that is insensitive to external disturbances. In addition, the sensor and the device must be able to calculate and continuously regulate the polymer concentration of the quenching bath.

SUMMARY OF THE INVENTION

These and other objects can be achieved by resolving the large number of difficulties faced in implementing such equipment, especially concerning the accuracy of guidance.

Such objects can be achieved with a viscosity sensor that operates on a principle of measurement that is based on the time taken by a piston centered in a measuring chamber of a calibrated tube immersed in a liquid bath to fall. The sensor is generally comprised of a lifting element that lifts up from a predetermined height in a mobile unit that includes the piston and at least one unit for transmitting movements of the piston. The mobile unit further includes a detection element, at its upper portion, which is primarily formed of a tubular body fixed to a rod associated with the transmitting unit, for example, at the center of a disk enclosing the tubular body. The detection element slides longitudinally inside a generally cylindrical measuring sensor which carries at least one detector for detecting movement of the detection element, and is lifted up by the lifting element using a finger which is fixed radially on the detection element and which traverses a longitudinal slit in the measuring sensor body.

Also provided is a device comprising the viscosity sensor and an electronic regulator that receives the information sent by the detector and that, through calculation, deduces the viscosity of the fluid. The device can further include a temperature detector so that the electronic regulator can calculate an equivalent viscosity which is brought down to a reference temperature, The electronic regulator is preferably able to calculate (by deduction) the concentration of a water/polymer mixture, depending on the type of polymer used, and to act on valves associated with the device to regulate and readjust the concentration of the bath according to the results obtained.

In the description which follows, such a device is referred to as a "drasticimeter", the structure of which will be more readily understood from the description which follows, with reference to the accompanying figures.

DETAILED DESCRIPTION OF THE INVENTION

Figure 3:
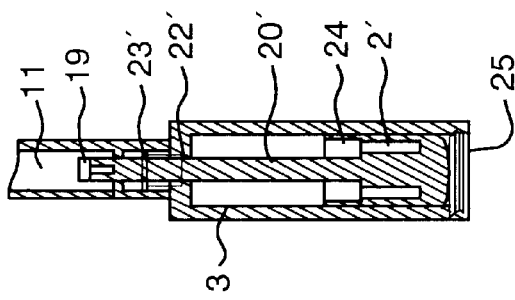
FIG. 3 is a partial, vertical cross-sectional view of a third embodiment of the device of the present invention.

In any of the exemplary embodiments shown in FIGS. 1 to 6, a drasticimeter is provided in accordance with the present invention which is primarily comprised of a viscosimeter (1) and an electronic regulator (31).

The viscosimeter (1) uses the known principle of measuring the time for a piston (2) to fall within a calibrated tube (3) which is immersed in the bath to be monitored. The piston is mechanically lifted by a cam (6) to allow liquid to be introduced into a measuring chamber (4) of the calibrated tube (3). The piston is then released, and falls by gravity. Liquid flowing back from the measuring chamber (4), or penetrating into the measuring chamber (4), then circulates in the space between the jacket of the calibrated tube (3) and the piston (2).

The cam (6) is driven in rotation by a back-geared motor (7) rotating, for example, at 1 rev/min, and operates to lift a mobile unit from a height (h) (shown in FIGS. 4A, 4B and 4C) of, for example, 50 mm. The mobile unit includes a detection part (8) at its top portion, the piston (2) which is centered in the chamber (4) at its lower portion, and a transmission unit (9) that transmits movement of the detection part to the piston. The set of elements including the back-geared motor (7), the cam (6) and the detection part (8) are covered by an enclosure (29).

The detection part (8) primarily includes a hollow tubular body (12) which is closed at its upper portion by a disk (10), the center of which receives the rod (11) of the transmission unit (9). The detection part (8) is guided for longitudinal sliding movement inside the generally cylindrical-shaped sensor body (12) by the disk (10) and a peripheral shoulder (13) which is machined on the body of the detection part (8). The detection part (8) is lifted by a finger (14) which is fixed radially in the disk (10) and which has an extremity which rests on the profile of the cam (6) through a longitudinal slit (15) for guiding the sensor body (12). The length of the slit is defined by the total drop (height) of the finger (14). The disk (10) and the shoulder (13) also perform a detection function. The disk (10) can alternatively be replaced by another peripheral shoulder (not shown).

A detector (16), for example, a non-contact proximity detector such as an inductive detector, is fixed to the sensor body (12) (see FIGS. 5A and 5B) to detect the passage of the shoulder (13) and the disk (10). By using a single detector for detecting two passages, differences potentially existing from one detector to another no longer constitute a problem.

Figure 4A:
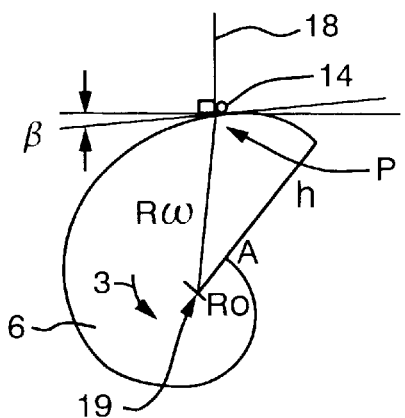
FIGS. 4A, 4B and 4C are schematic representations of the drive cam of a mobile detection part used in the embodiments of FIGS. 1 to 3.
Figure 4B:
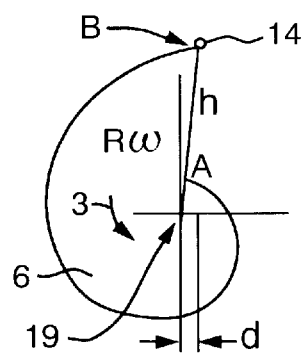
Figure 4C:
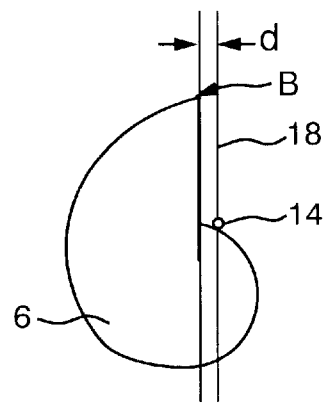
Figure 5A:
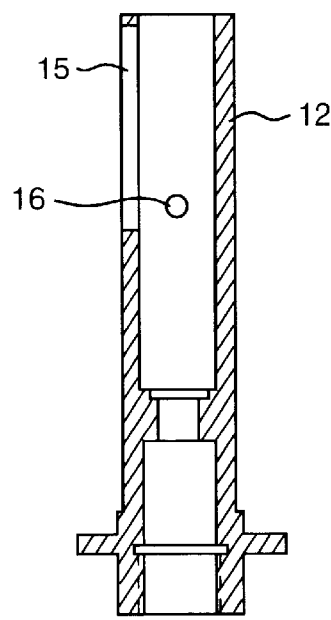
FIGS. 5A and 5B are vertical cross-sectional views showing details of the sensor body which slidingly receives the detection part.
Figure 5B:
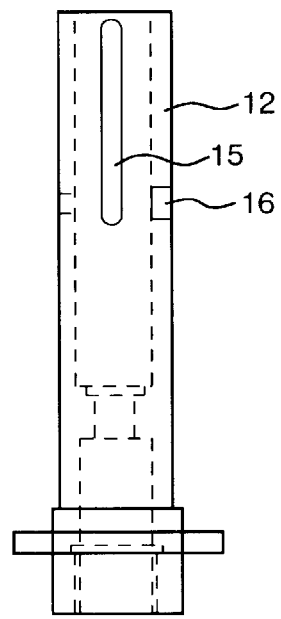

FIG. 4A schematically shows lifting of the finger (14) by rotation of the cam (6). After a full revolution, the finger (14) is moved through a maximum height (see FIG. 4B) and quickly falls from the point (B) to the point (A) (see FIG. 4C), driven by the weight of the piston and of the lifting system. To function properly, it is necessary to offset the lifting spindle (18) and the spin axis of the cam (19) by a distance (d) (see FIGS. 4B and 4C). This makes it possible to avoid extreme cases where the tested mixture would be slightly viscous, and where the fall of the piston would be too quick, causing the finger to fall onto the flat portion of the cam instead of falling to the point (A). An optimum value for the distance (d) has been determined experimentally, where the finger (14) instantly falls from (B) to (A) without touching the flat portion of the cam (see FIGS. 4B and 4C).

Moreover, the profile of the cam is calculated so that, during a cycle, the finger (14) rises regularly on the lifting spindle (18) and the tangent of the cam at the contact point (P) is as close as possible to normal at the lifting spindle (18) (see FIG. 4A). To achieve this, the cam profile has been calculated so that the attack angle $\beta$ under the finger (14) is virtually constant (see FIG. 4A). At any point of the cam profile, the radius $R\omega$ is calculated according to the following formula:

$$R\omega = Ro(1+e)^6,$$

with $$e = \left(\frac{Ro+h}{Ro}\right)\frac{1}{2\pi_{-1}}$$

where: Ro=the initial radius at the start point (A) of a cycle;
h=the distance between the start point (A) and the extreme point (B) of a cam cycle; and
$\omega$=the angle of rotation of the cam.

Figure 1:
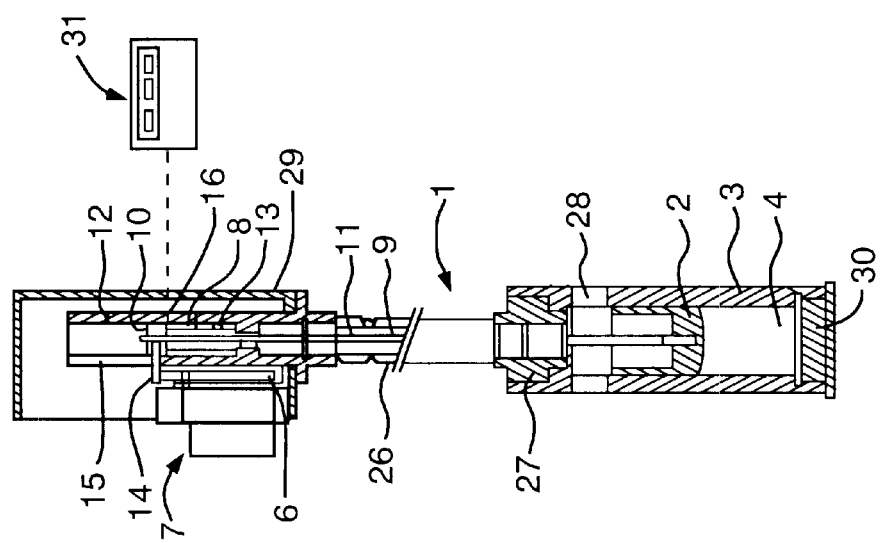
FIG. 1 is a vertical cross-sectional view of a first embodiment of the device of the present invention.

A first embodiment of the transmission unit (9) is shown in FIG. 1, and is comprised of a rod (11) having a bottom extremity which is screwed directly into the piston (2). A tube (26), which has first been screwed beneath the body of the sensor (8), and then onto the stopper (27) of the calibrated tube (3), ensures a rigid link between the calibrated tube and the motor elements, and also ensures proper sealing.

The measuring chamber (4) isolates the quantity of liquid used for the measurements to be made, and places the liquid away from eddies and other disturbances due to agitation of the bath. Two orifices (28), which are preferably formed in the side of the tube (3), make it possible to regenerate the measuring liquid. The calibrated tube (3) has a closed bottom, either formed as a unitary structure or as a removable stopper 30.

The embodiment of FIG. 1 requires a clear vertical fall along its axis, and pointed machinings and centerings to avoid drifting.

Figure 2:
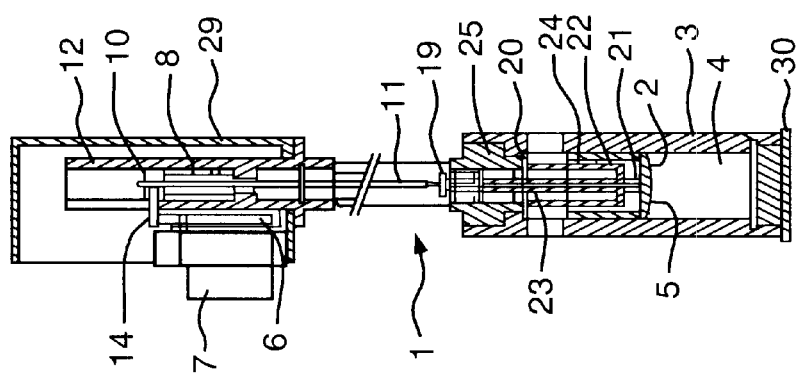
FIG. 2 is a vertical cross-sectional view of a second embodiment of the device of the present invention.

A second embodiment of the transmission unit (9) is shown in FIG. 2, and avoids the need for guidance along the entire length of the transmission unit. In this configuration, the rod is joined to guide only the lower portion of the unit. To this end, the rod (11) is joined by a swivel pin (19) to the upper extremity of a transmission tube (20) having a foot (21) which is screwed to the bottom of the piston (2) by screws (5). The tube (20) could also be screwed to the bottom of the piston, as in the first embodiment of FIG. 1. The transmission tube (20) is guided between two horizontal planes embodied by two annular edges (22) and (23) inside a tubular guide (24) having a head (25) which closes the measuring chamber (4). This embodiment does not have the potential of the preceding embodiment for drifting.

A third embodiment of the transmission unit (9) is shown in FIG. 3 and includes, as in the preceding embodiment, a joint (19) between the transmission rod (11) and the transmission tube (20'), forming a single unit with the piston (2'). Perforations (24) are provided to lighten the piston (2'). Guidance is provided by two annular edges (22') and (23') formed directly in the body of the calibrated tube (3). The calibrated tube (3) is closed at its lower portion by a stopper (25), using circlips. This third embodiment operates well and, moreover, needs less machining to produce.

Figure 8:
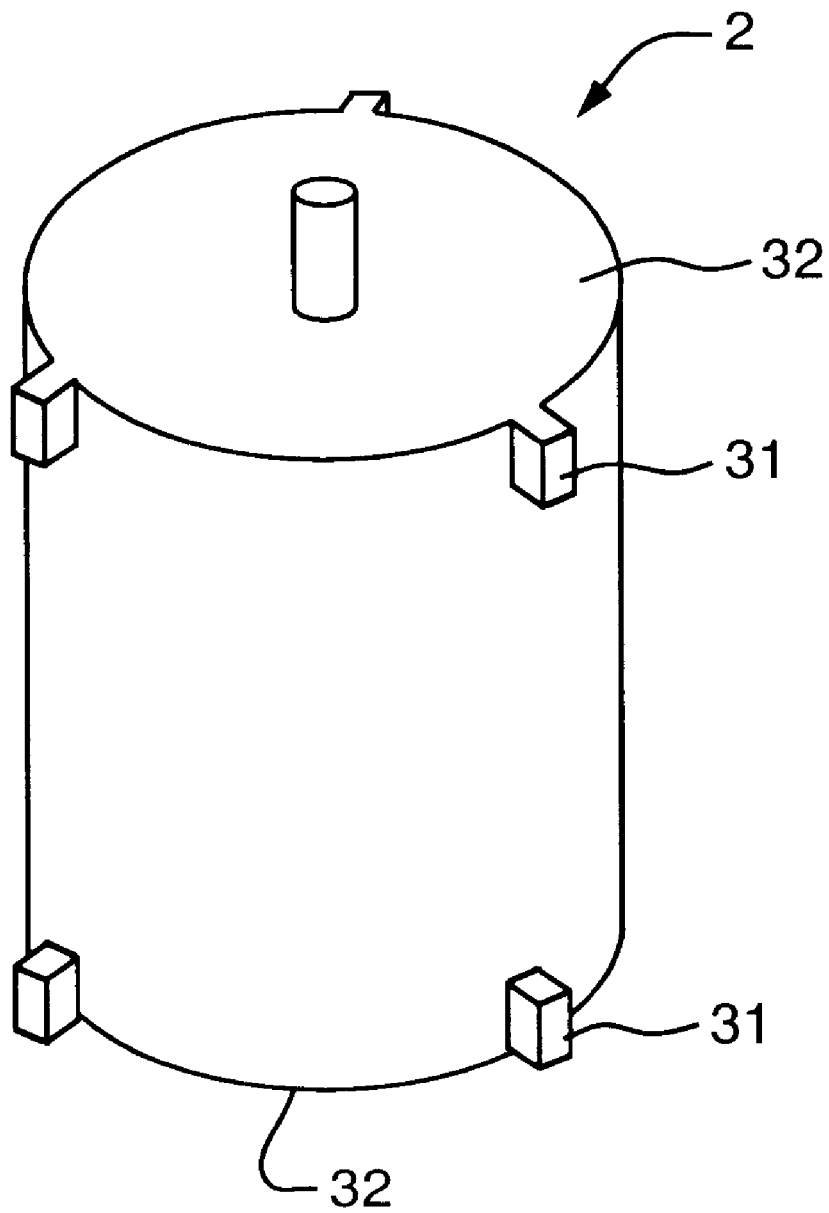
FIG. 8 is an isometric view of a piston showing an alternative guiding structure.

Referring to FIG. 8, the cylindrical piston (2) is fitted with at least two crowns (32) including centering points (31). The crowns (32) are distributed over the height of the piston, usually including one crown on the upper diameter and another crown on the lower diameter. Each of the crowns (32) includes at least three centering points (31) distributed on the circumference of the piston, for example, a series of three centering points separated by an angle of 120°. The centering points (31) are formed as small surfaces, measuring several mm, and are received in a cylinder having a diameter slightly smaller than that of the chamber to coaxially position the piston in the chamber with a minimum amount of rubbing. The upper portion of the piston is supported by the linking rod (11), at the detection part (8), the linking rod no longer being guided in the linking tube (26).

Figure 6:
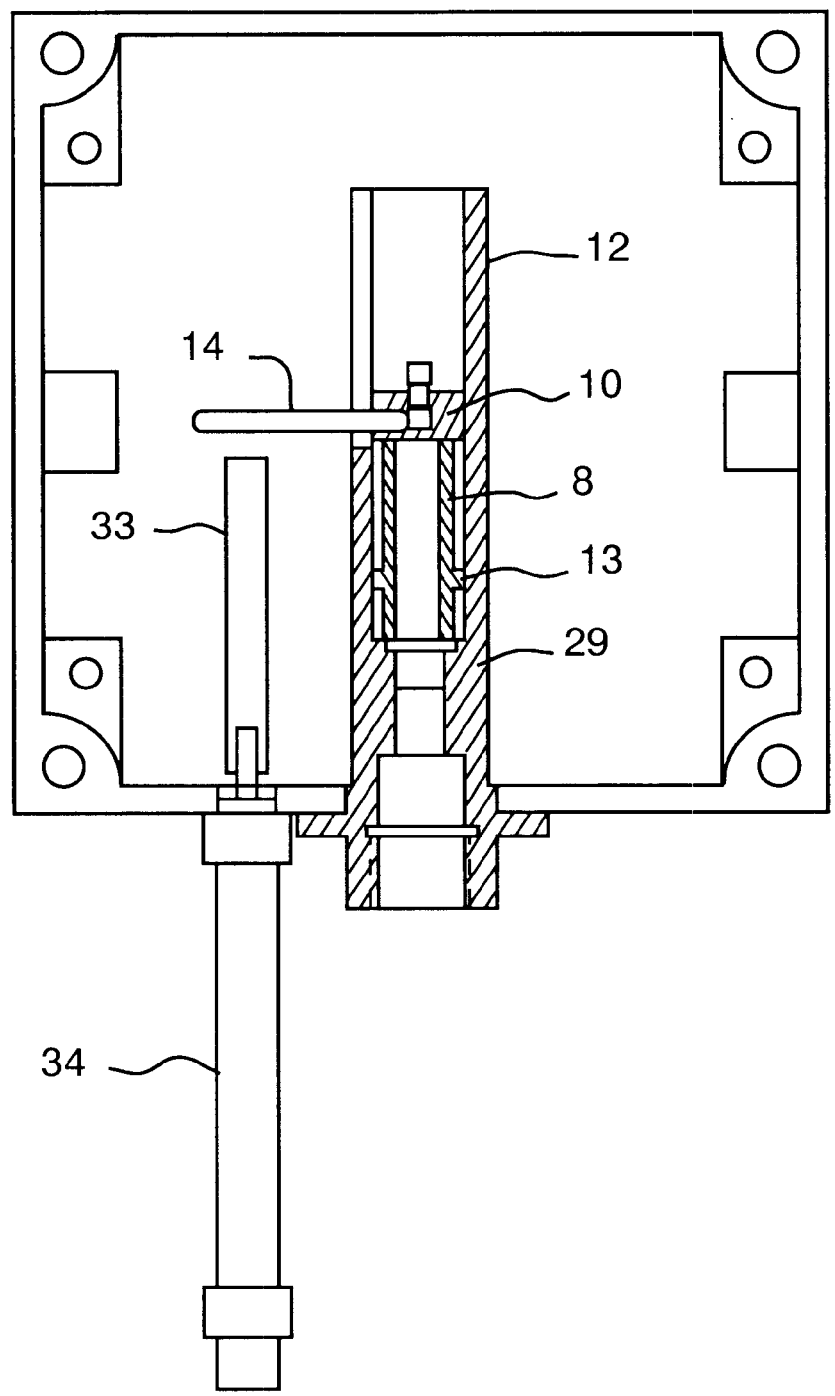
FIG. 6 is a partial, vertical cross-sectional view of an alternative embodiment of the invention having a pneumatic drive.

In the alternative embodiment shown in FIG. 6, the finger (14) is lifted by the rod (33) of a dual effect jack (34), which is pneumatically. controlled. This "anti-exploding" version can be used in petrochemical applications.

Figure 7:
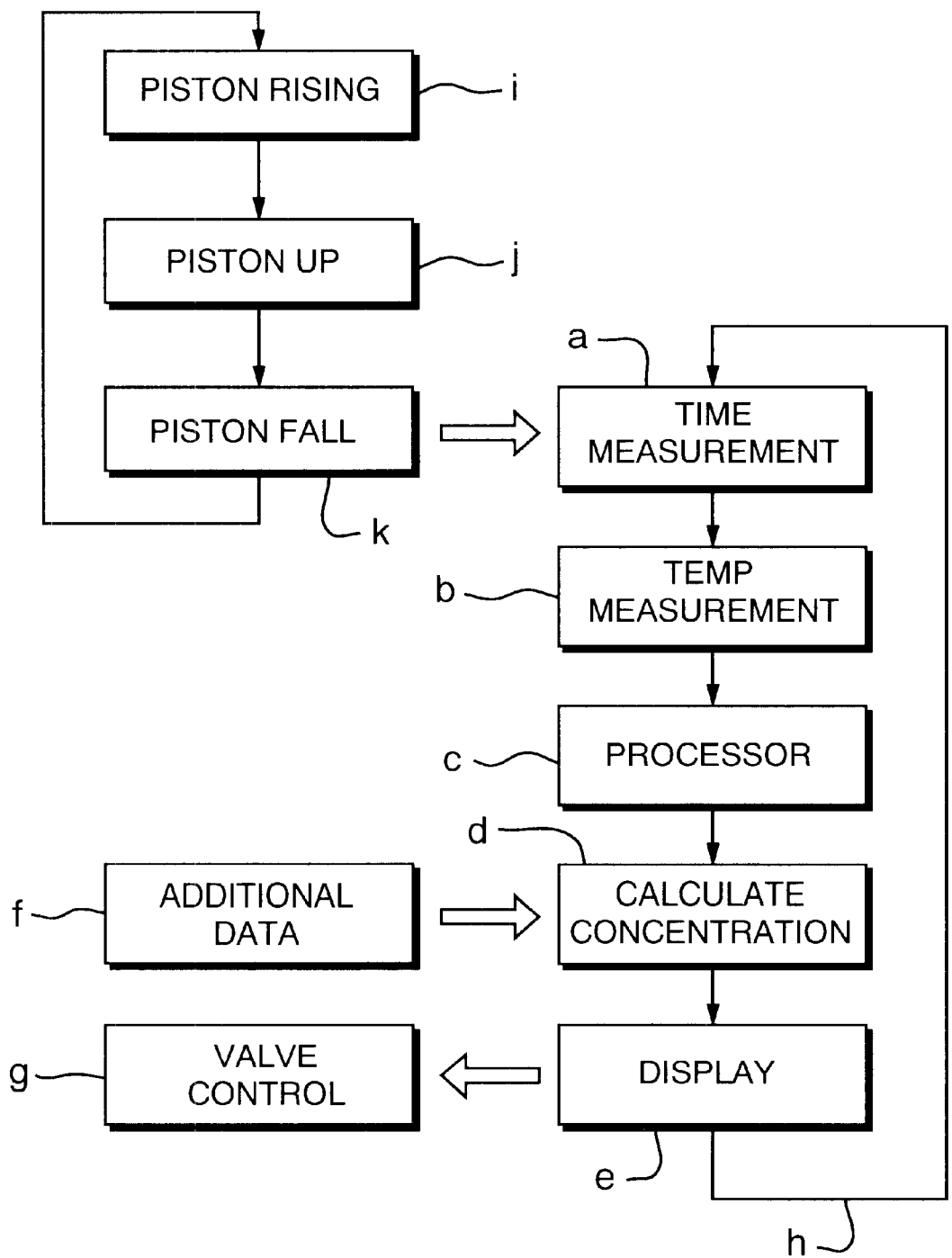
FIG. 7 is a flow chart of an operating cycle of the device of the present invention.

FIG. 7 describes an operational cycle of the device to provide a description of the principle by which the regulator (31) operates. For each cycle, signals responsive to rising of the piston (i), arrival of the piston in its upper position (j) and fall of the piston (k), as well as the time measurements (a) recorded by the detector (16) and temperature measurements (b) of the bath, which can be recorded with a known temperature detector (not shown), are sent to a processor (c) associated with the regulator (31). After conversion, the data is displayed on a display unit and/or recorded by a recording device (not shown).

The device is first calibrated by testing with various water/polymer mixtures at various temperatures, or by comparison with viscosity measurements conducted with a calibrated viscosimeter. The processor then deduces, by calculations of the processor (c), the viscosity of the mixture and the equivalent viscosity brought down to a reference temperature (for example, 20° C.).

By providing the regulator (31) with additional data (f) corresponding to the nature of the polymer, the regulator (31) can calculate the concentration (d) of the mixture used (e.g., 20% PAG in 80% water).

A display unit (e) is provided to display information such as the temperature of the bath, the fall time measured for the piston, the viscosity of the bath at its actual temperature, the viscosity of the bath brought down to 20° C., and the polymer concentration. Depending upon the results obtained, it is also possible to provide actions (g) for controlling valves associated with the bath system, to regulate and readjust the concentration, and to again measure the fall time measured for the piston (the loop h).

What is claimed is:

1. A viscosity sensor for measuring the fall of a piston immersed in a liquid bath, comprising:
    a calibrated tube defining a measuring chamber and receiving the piston, wherein the piston is centered in the measuring chamber of the calibrated tube; and
    a lifting element for lifting a mobile unit to a defined height, wherein the mobile unit includes the piston, at least one transmission unit coupled with the piston for transmitting movement of the lifting element to the piston, and a detection part associated with an upper portion of the mobile unit;
    wherein the detection part is formed as a tubular body fixed to a rod coupled with the transmission unit;
    wherein the detection part slides longitudinally inside a generally cylindrical measuring sensor body having a single detector for detecting passage of two shoulders provided on the detection part; and
    wherein the detection part is lifted up by the lifting element responsive to a finger which is radially fixed to the detection part and which traverses a longitudinal slit provided in the measuring sensor body.

2. The viscosity sensor of claim 1 wherein the tubular body is closed at the upper portion by a disk having a center which fixedly receives the rod.

3. The viscosity sensor of claim 2 wherein the finger is fixed to the disk.

4. The viscosity sensor of claim 2 wherein the tubular body is hollow.

5. The viscosity sensor of claim 2 wherein the disk forms a first one of the two shoulders provided on the detection part.

6. The viscosity sensor of claim 5 wherein a second one of the two shoulders provided on the detection part is a peripheral shoulder formed on the tubular body of the detection part.

7. The viscosity sensor of claim 1 wherein the detector is a non-contact proximity detector.

8. The viscosity sensor of claim 1 wherein the rod threadingly engages the piston.

9. The viscosity sensor of claim 1 wherein the piston includes at least two crowns, and wherein each of the crowns includes at least three centering points for coaxially positioning the piston in the measuring chamber.

10. The viscosity sensor of claim 1 wherein the rod is joined by a swivel pin to upper portions of a transmission tube which is guided between a pair of annular edges.

11. The viscosity sensor of claim 10 wherein bottom portions of the transmission tube include a foot which threadingly engages the piston, and wherein the pair of annular edges are located inside a tubular guide having a head which closes the measuring chamber.

12. The viscosity sensor of claim 11 wherein the transmission tube is unitary with the piston, and wherein the pair of annular edges are provided in the body of the calibrated tube.

13. The viscosity sensor of claim 1 which further includes a linking tube coupling the measuring sensor body and the piston.

14. The viscosity sensor of claim 1 wherein the lifting element includes a pneumatic jack having a push rod for engaging the finger, and for lifting the finger.

15. The viscosity sensor of claim 14 wherein the push rod engages the finger for lifting the finger by a defined height on a lifting spindle.

16. The viscosity sensor of claim 1 wherein the lifting element includes a cam which is rotated in a vertical plane and which has a cam profile for receiving the finger.

17. The viscosity sensor of claim 16 wherein the cam is driven in rotation by a back-geared motor.

18. The viscosity sensor of claim 16 wherein the cam is rotated through a complete revolution, wherein the cam profile extends between a start position and a maximum height position, and wherein the finger engaging the cam profile is caused to fall to the start position after passing the maximum height position by following a lifting spindle.

19. The viscosity sensor of claim 18 wherein the cam has a spin axis, and wherein the lifting spindle is offset with respect to the spin axis of the cam by a defined distance.

20. The viscosity sensor of claim 16 wherein the cam profile is defined according to the formula:

$$R\omega = Ro(1+e)^6,$$

with $$e = \left(\frac{Ro+h}{Ro}\right)\frac{1}{2\pi_{-1}}$$

where: Ro=an initial radius at a start point (A) of a cycle;
h=a distance between the start point (A) and an extreme point (B) of the cycle; and
$\omega$=an angle of rotation of the cam.

21. A device for continuously measuring viscosity in a liquid bath, comprising:
a viscosity sensor for measuring the fall of a piston immersed in the liquid bath, including a calibrated tube defining a measuring chamber and receiving the piston, wherein the piston is centered in the measuring chamber of the calibrated tube, and a lifting element for lifting a mobile unit to a defined height, wherein the mobile unit includes the piston, at least one transmission unit coupled with the piston for transmitting movement of the lifting element to the piston, and a detection part associated with an upper portion of the mobile unit; wherein the detection part is formed as a tubular body fixed to a rod coupled with the transmission unit, wherein the detection part slides longitudinally inside a generally cylindrical measuring sensor body having a single detector for detecting passage of two shoulders provided on the detection part, and wherein the detection part is lifted up by the lifting element responsive to a finger which is radially fixed to the detection part and which traverses a longitudinal slit provided in the measuring sensor body; and
an electronic regulator coupled with the detector, wherein the electronic regulator receives data from the detector, and wherein the electronic regulator includes a processor for calculating the viscosity of the liquid bath.

22. The device of claim 21 which further includes a temperature detector, and wherein the processor additionally calculates an equivalent viscosity brought down to a reference temperature.

23. The device of claim 21 wherein the liquid bath is a polymer/water mixture including a selected polymer type and mixed in a defined concentration, and wherein the processor additionally calculates the concentration of the polymer/water mixture according to the type of the polymer.

24. A device for continuously controlling a liquid bath, wherein the liquid bath has a defined concentration and viscosity, comprising:
a viscosity sensor for measuring the fall of a piston immersed in the liquid bath, including a calibrated tube defining a measuring chamber and receiving the piston, wherein the piston is centered in the measuring chamber of the calibrated tube, and a lifting element for lifting a mobile unit to a defined height, wherein the mobile unit includes the piston, at least one transmission unit coupled with the piston for transmitting movement of the lifting element to the piston, and a detection part associated with an upper portion of the mobile unit;
wherein the detection part is formed as a tubular body fixed to a rod coupled with the transmission unit, wherein the detection part slides longitudinally inside a generally cylindrical measuring sensor body having a single detector for detecting passage of two shoulders provided on the detection part, and wherein the detection part is lifted up by the lifting element responsive to a finger which is radially fixed to the detection part and which traverses a longitudinal slit provided in the measuring sensor body; and
an electronic regulator coupled with the detector and at least one valve coupled with the liquid bath for regulating and readjusting the concentration of the liquid bath, wherein the electronic regulator receives data from the detector, wherein the electronic regulator includes a processor for calculating the viscosity of the liquid bath, and wherein the electronic regulator controls the valve to regulate and readjust the concentration of the liquid bath according to the calculated viscosity.

* * * * *